(12) United States Patent
Bishop

(10) Patent No.: US 8,633,258 B2
(45) Date of Patent: Jan. 21, 2014

(54) D1492 LIQUID BAPO PHOTOINITIATOR AND ITS USE IN RADIATION CURABLE COMPOSITIONS

(75) Inventor: Timothy Edward Bishop, Algonquin, IL (US)

(73) Assignee: DSM IP Assets B.V., Heerlen (NL)

( * ) Notice: Subject to any disclaimer, the term of this patent is extended or adjusted under 35 U.S.C. 154(b) by 190 days.

(21) Appl. No.: 13/388,737

(22) PCT Filed: Jun. 21, 2011

(86) PCT No.: PCT/US2011/041150
§ 371 (c)(1),
(2), (4) Date: Feb. 3, 2012

(87) PCT Pub. No.: WO2012/012067
PCT Pub. Date: Jan. 26, 2012

(65) Prior Publication Data
US 2012/0129968 A1 May 24, 2012

Related U.S. Application Data

(60) Provisional application No. 61/359,944, filed on Jun. 30, 2010.

(30) Foreign Application Priority Data

Jul. 16, 2010 (EP) .................... 10169846

(51) Int. Cl.
| | | |
|---|---|---|
| *A61K 6/083* | (2006.01) | |
| *C08F 2/50* | (2006.01) | |
| *C08B 37/00* | (2006.01) | |
| *C08F 2/46* | (2006.01) | |
| *B29C 71/04* | (2006.01) | |
| *C08G 61/04* | (2006.01) | |

(52) U.S. Cl.
USPC ............ 522/18; 522/12; 522/7; 522/6; 522/1; 522/71; 520/1

(58) Field of Classification Search
USPC .......................... 522/18, 12, 7, 6, 1, 71; 520/1
See application file for complete search history.

(56) References Cited

U.S. PATENT DOCUMENTS

| 5,472,992 A * | 12/1995 | Leppard et al. ................ 522/18 |
| 6,246,824 B1 | 6/2001 | Vandeberg et al. |
| 2001/0031898 A1 | 10/2001 | Wolf et al. |
| 2008/0004464 A1 | 1/2008 | Murer et al. |

FOREIGN PATENT DOCUMENTS

| CN | 1175583 A | 3/1998 |
| CN | 101484515 A | 7/2009 |
| WO | WO 2007/087259 | 8/2007 |
| WO | WO 2010/060702 | 6/2010 |
| WO | WO 2012/012067 A1 | 1/2012 |

OTHER PUBLICATIONS

International Search Report for PCT/US2011/041150, mailed Oct. 19, 2011.
International Search Report and Written Opinion from PCT with mailing date of Oct. 19, 2011 in connection with International Application No. PCT/US2011/141150; 9 pages.
European Search Report dated Jan. 26, 2011 issued in European Appln. No. 10169846.2; 6 pages.
Kamai, G. et al: "The Effect of Anhydrides of Organic Acids on Trialkyl Phosphites and Sodium Dialkyl Phosphites", Journal of General Chemistry of the USSR, vol. 27, (Published 1957), pp. 1030-1033.
Office Action in related Chinese Patent Application No. 201180003178.6; Date of Issue: Sep. 5, 2013; 14 pages; In Chinese with English Translation.
International Preliminary Report on Patentability and Written Opinion from PCT with Issuance Date of Jan. 8, 2013 in connection with International Application No. PCT/US2011/041150; 7 pages.
Kamai et al.: "The Effect of Anhydrides of Organic Acids on Trialkyl Phospites and Sodium Dialkyl Phospites", Journal of General Chemistry of the USSR; vol. 27, (1957), pp. 1030-1033.

* cited by examiner

*Primary Examiner* — Ling Choi
*Assistant Examiner* — Jessica E Whiteley
(74) *Attorney, Agent, or Firm* — Nixon & Vanderhye P.C.

(57) ABSTRACT

The invention relates to a liquid bis(acyl)phosphine oxide of formula (I): wherein R is $C_1$-$C_{18}$ alkyl, and wherein R is optionally substituted as described herein. The invention also relates to radiation curable compositions comprising liquid bis(acyl)phosphine oxide of formula (I).

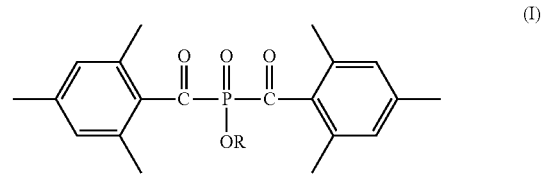

(I)

19 Claims, No Drawings

D1492 LIQUID BAPO PHOTOINITIATOR AND ITS USE IN RADIATION CURABLE COMPOSITIONS

This application is the U.S. national phase of International Application No. PCT/US2011/041150, filed 21 Jun. 2011, which designated the U.S. and claims the benefit of U.S. Provisional Application No. 61/359,944, filed 30 Jun. 2010, and claims priority to EP Application No. 10169846.2, filed 16 Jul. 2010, the entire contents of each of which are hereby incorporated by reference.

FIELD OF THE INVENTION

The invention relates to liquid bis(acyl)phosphine oxide photoinitiators and radiation curable compositions comprising said photoinitiators.

BACKGROUND OF THE INVENTION

Radiation curable coating compositions are used in many industries including, but not limited to fiber optic materials and coatings for various substrates such as concrete, metal, ceramic, glass, plastic, composites and textiles. Common types of radiation curable compositions are those compositions curable by free radical polymerization. In these compositions, the radiation (e.g., UV radiation) is absorbed by the composition to effect curing or polymerization via the generation of free radicals. The curing of the composition is accomplished by photoinitiators, which absorb the UV energy and react to generate free radicals, which in turn react with double bonds in the composition (e.g., acrylate groups) to form new free radicals (i.e., the initiation step). The newly formed free radicals then react with other double bond centers to polymerize or cure (i.e., solidify) the uncured, liquid composition in the propagation step. Eventually, the polymerization reaction is terminated when the free radicals react with other free radicals instead of reacting with other reactive sites to form new free radicals. This step is aptly referred to as the termination step. In view of the foregoing, it is apparent that the choice of photoinitiator is important to the success of a free radical polymerization process.

A review of photoinitiators for UV curing is disclosed in "A Compilation of Photoinitiators Commercially Available for UV Today" by Dr. Kurt Dietliker of Ciba Specialty Chemicals PLC published by SITA Technology Limited (2002), which is incorporated herein by reference in its entirety. In April 2009, Ciba Holding AG was acquired by BASF.

Radiation-curable compositions are extensively used in the optical fiber industry during the production of optical fibers, ribbons and cables. For example, optical glass fibers are routinely coated with at least two radiation-curable coatings immediately after the glass fiber is manufactured in a draw tower so as to preserve the pristine character of the glass fiber and protect it sufficiently such that it can be collected on a round spool. Immediately after a coating is applied to the fiber, the coating is rapidly cured by exposure to radiation (commonly ultraviolet light). Currently, the industry demands faster production speeds and therefore, faster curing coating compositions.

Radiation-curable up-jacketing, matrix and bundling materials can further support and protect the individual strands of coated fiber as individual strands are bundled together into optical fiber ribbons, optical fiber cables and associated structures. In addition, radiation-curable inks can be used to color code individual strands of optical fiber. All of these types of optical fiber-related materials are radiation-curable and can serve as coating and/or cabling materials.

Examples of radiation-curable inner primary coatings are disclosed in U.S. Pat. No. 5,336,563 to Coady et al. and of outer primary coatings (e.g., secondary coatings) in U.S. Pat. No. 4,472,019 to Bishop et al. Additional aspects of optical fiber coating technology are disclosed in, for example, U.S. Pat. No. 5,595,820 to Szum; U.S. Pat. No. 5,199,098 to Nolan et al.; U.S. Pat. No. 4,923,915 to Urruti et al.; U.S. Pat. No. 4,720,529 to Kimura et al.; and U.S. Pat. No. 4,474,830 to Taylor et al., each of which is incorporated herein by reference in their entirety.

The following U.S. Patent Applications, describing and claiming illustrative radiation curable coating compositions, are incorporated by reference in their entirety: U.S. patent application Ser. No. 11/955,935, filed Dec. 13, 2007, published as US 20080226916 on Sep. 19, 2008; U.S. patent application Ser. No. 11/955,838, filed Dec. 13, 2007, published as US 20080241535 on Oct. 23, 2008; U.S. patent application Ser. No. 11/955,547, filed Dec. 13, 2007, published as US 20080226912 on Sep. 19, 2008; U.S. patent application Ser. No. 11/955,614, filed Dec. 13, 2007, published as US 20080226914 on Sep. 19, 2008; U.S. patent application Ser. No. 11/955,604, filed Dec. 13, 2007, published as US 20080226913 on Sep. 19, 2008; U.S. patent application Ser. No. 11/955,721, filed Dec. 13, 2007, published as US 20080233397 on Sep. 25, 2008; U.S. patent application Ser. No. 11/955,525, filed Dec. 13, 2007, published as US 20080226911 on Sep. 19, 2008; U.S. patent application Ser. No. 11/955,628, filed Dec. 13, 2007, published as US 20080226915 on Sep. 19, 2008; and U.S. patent application Ser. No. 11/955,541, filed Dec. 13, 2007, published as US 20080226909 on Sep. 19, 2008.

Radiation-curable coatings are used as coatings for concrete and metal. UV curable concrete coatings are discussed, for example, in the article, "UV Curable Concrete Coatings" by Jo Ann Arceneaux, Ph.D., Cytec Industries Inc., Smyrna, Ga., presented at the Federation of Societies for Coatings Technology, "Coatings for Concrete Conference: "Coating the World of Concrete," on Feb. 2, 2009 at the Westin Casuarina Las Vegas Hotel in Las Vegas, Nev. and in the article, "Field-Applied, UV-Curable Coatings for Concrete Flooring," by Peter T. Weissman, published in the January/February/March 2009 RADTECH Report.

UVolve® Instant Floor Coatings (available from DSM), are high performance, instant cure coating systems for concrete floors which have the following features and benefits:

virtually instantly curing ability allows for immediate traffic—even forklift;

one-component system with no mixing, with no pot life constraints or wasted product;

the cured coating protects concrete against damage from dirt, wear and chemicals; and cured UVolve® Instant Floor Coatings clean easily—especially forklift tire marks.

The use of radiation curable coatings for concrete floors means that the facility maintenance costs will be lower due to easy clean. UVolve® Instant Floor Coatings have zero VOC, no solvents, and 100% solids. UVolve® Instant Floor Coatings cure to a high gloss, durable finish which exhibits excellent scratch and impact resistance. They are available in both clear and pigmented systems and cure instantly with the use of a UV light machine specifically designed for use with UVolve® Instant Floor Coatings. See: http://www.uvolve-coatings.com/.

The UVaCorr® Corrosion-Resistant UV Coatings for Tube & Pipe (UVaCorr® products are available from DSM), are high performance, radiation curable coating systems used to improve the corrosion resistance of tube and pipe. The UVaCorr® coatings are available as both clear and colored coatings and are used to protect tube and pipe during storage and transport. The UVaCorr® product line, now certified for use in the Venjakob™ Ven Spray Pipe system(trademark of Venjakob), boast several performance advantages over traditional solvent-based and water-borne tube & pipe coatings, including: instant cure for high-speed processing; 100% solid coatings for higher applied coverage and no VOC's; better salt spray resistance for enhanced performance; and smaller equipment footprint with reduced energy requirements. See: http://www.dsm.com/en_US/html/dsmd/uvention_tube.htm To maximize cure speed in an ultraviolet light cure, at least one photoinitiator is required (photoinitiator may be omitted in an electron beam cure). Several photoinitiators can be used to achieve a suitable balance of surface and through cure. For further discussion of the use of more than one photoinitiator see U.S. Pat. Nos. 6,438,306 and 7,276,543. When more than one photoinitiator is present in a radiation curable composition of the invention, conventional classes of photoinitiators have been found to be useful.

Solid mono-acyl phosphine oxide type photoinitiators can be used, such as LUCIRIN™ TPO (2,4,6-trimethylbenzoyl) diphenyl phosphine oxide, available commercially from BASF, which exhibits relatively fast cure speed. However, use of solid, commercial LUCIRIN™ TPO can cause undesired crystallization effects in coating compositions (e.g., during aging), which can result in occlusions and loss of optical clarity (detected under a light microscope).

Certain photoinitiators are known to cause yellowing, particularly during long term aging of cured compositions under photolytic aging conditions (e.g., UV or fluorescent light). Heat may also induce yellowing. Discoloration in general and yellowing in particular is undesirable and has become anathema in the industry. Hence, a photoinitiator which would lack harmful crystalline effects and still effect fast cure, but would result in yellowing, would not sufficiently meet the most stringent industry demands.

Attempts have been made to use purified LUCIRIN™ TPO, but the purification steps are costly. Other solid phosphine oxide photoinitiators (e.g., CGI 403, Ciba) can show reduced amounts of harmful crystallization effect, but they may also have slower cure speed. Hence, it is desirable to provide photoinitiators which can provide both fast cure speed and good optical clarity.

Other desirable performance properties for radiation curable media include: being a liquid at ordinary temperatures and having a sufficiently low viscosity to be excellently coated; providing good productivity at a high curing rate; having sufficient strength and superior flexibility; exhibiting very little physical change during temperature changes over a wide range; having superior heat resistance and superior resistance to hydrolysis; showing superior long term reliability with little physical changes over time; showing superior resistance to chemicals such as acids and alkalis; exhibiting low moisture and water absorption; exhibiting superior light resistance showing the least discoloration over time; and exhibiting high resistance to oils. Moreover, an increased demand for processing speed of cured materials makes it necessary for the coating compositions to cure quickly in a stable manner. Thus, a photoinitiator(s) which decomposes fast must be used for the coating materials to cure quickly.

As of the filing date of the instant application, the art is yet to recognize a photoinitiator which provides an excellent balance of all of these critical properties. For example, a large number of phosphine oxide photoinitiators are disclosed in, for example, U.S. Pat. No. 5,218,009 to Rutsch et al. and U.S. Pat. No. 5,534,559 to Leppard et al. However, these patents do not suggest that any particular species of photoinitiators would solve the above-identified problems and provide an excellent balance of properties.

Japanese Patent Application Laid-open No. 190712/1989 discloses a composition comprising an acyl phosphine oxide as a photo-curable resin composition which realizes high productivity in fast curing. However, this composition is not necessarily cured at a high enough rate to sufficiently increase the productivity of optical fibers while maintaining the characteristics required for an optical fiber coating material.

Another composition comprising a bis-acyl phosphine oxide has been proposed in Japanese Patent Application Laid-open No. 259642/1996 as a photo-curable resin composition which shows high productivity by being cured at a high rate. However, the bis-acyl phosphine oxide containing a long chain aliphatic group disclosed in this Japanese Patent Application has a poor solubility in resin compositions, and hence cannot be dissolved in the resin compositions in an amount sufficient to ensure a high cure rate.

U.S. Pat. Nos. 6,136,880 and 6,359,025 and EP Patent Application EP 0975693 to Snowwhite et al. disclose radiation curable coating compositions for optical fiber comprising solid bis-acylphosphine oxide (BAPO) type photoinitiators.

Bis-acylphosphine oxide (i.e., bis(2,4,6-trimethylbenzoyl) phenylphosphine oxide) (BAPO) is a very potent photoinitiator in radiation curable compositions light-induced polymerization of the ethylenically unsaturated compounds. It has a higher extinction coefficient than acyl phosphine oxides such as TPO or TPO-L and thus typically leads to superb photo speed. However, BAPO is a solid having a low solubility in a variety of monomers and oligomers, which limits its use in some applications.

In an attempt to address the shortcomings of solid BAPO, liquid photoinitiator mixtures of BAPO with bis-acylphosphine (BAP) have been reported. For example, see "Liquid Bis-Acylphosphine Oxide (BAPO) Photoinitiators" by C. C. Chiu from Chitec Technology presented at RADTECH 2010 on Monday, May 24, 2010.

In the Chiu presentation, liquid mixtures of BAPO and BAP (collectively known as "LMBAPO") are described. Although the liquid mixture of BAPO and BAP photoinitiators (i.e., LMBAPO) purportedly has film-curing properties similar to solid BAPO, LMBAPO suffers from poor chemical stability, which limits its industrial application.

Thus, there remains an unmet need for photoinitiators suitable for radiation curable compositions exhibiting a balance of the critical performance properties, including existing in a liquid state for radiation curable compositions.

BRIEF SUMMARY OF THE INVENTION

In a first embodiment, the invention provides a liquid bis (acyl)phosphine oxide of formula (I):

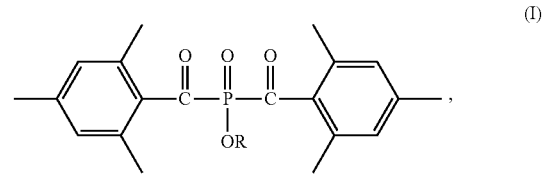

wherein R is $C_1$-$C_{18}$ alkyl, and wherein R is optionally substituted.

In a second embodiment, the invention provides a radiation curable composition comprising a liquid bis(acyl)phosphine oxide of formula (I).

In a third embodiment, the invention provides a bis(acyl) phosphine oxide of formula (I):

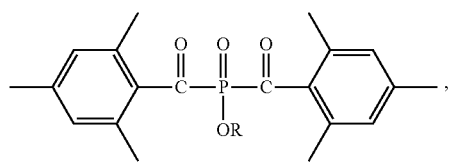

(I)

wherein R is $C_1$-$C_{18}$ alkyl, and wherein R is optionally substituted, which bis(acyl)phosphine oxide is liquid at 20° C.

In a fourth embodiment, the invention provides a bis(acyl) phosphine oxide of the third embodiment, wherein R is $C_1$-$C_6$ alkyl, and wherein preferably R is selected from the group consisting of methyl, ethyl, n-propyl, 2-propyl, n butyl, sec-butyl, t-butyl, and hexyl.

In a fifth embodiment, the invention provides a bis(acyl) phosphine oxide of third embodiment, wherein R is $C_1$-$C_3$ alkyl, and wherein preferably R is selected from the group consisting of methyl, ethyl and n-propyl, more preferably R is ethyl.

In a sixth embodiment, the invention provides a radiation curable composition comprising the bis(acyl)phosphine oxide of any one of the third through fifth embodiments and at least one free-radical polymerizable component.

In a seventh embodiment, the invention provides a radiation curable composition of the sixth embodiment, wherein said composition is selected from the group consisting of an optical fiber coating composition and a coating composition capable of radiation cure on concrete and a coating composition capable of radiation cure on metal.

In an eighth embodiment, the invention provides a optical fiber coating composition of the seventh embodiment, wherein the optical fiber coating composition is selected from the group consisting of a primary coating, a secondary coating, an ink coating, an up-jacketing coating, a buffer coating and a matrix coating.

In a ninth embodiment, the invention provides a radiation curable composition of any one of the sixth through eighth embodiments, wherein the composition is curable by UV light generated by a conventional UV light source.

In a tenth embodiment, the invention provides a radiation curable composition of any one of the sixth through ninth embodiments, wherein the composition is curable by light generated by a LED light source.

In an eleventh embodiment, the invention provides a radiation curable composition of any one of the sixth through tenth embodiments, wherein the composition further comprises at least one additional photoinitiator.

In a twelfth embodiment, the invention provides a radiation curable composition of the eleventh embodiment, wherein the at least one additional photoinitiator is selected from the group consisting of photoinitiators that are solid at 20° C. and photoinitiators that are liquid at 20° C.

In a thirteenth embodiment, the invention provides a radiation curable composition of the twelfth embodiment, wherein the solid photoinitiators are selected from the group consisting of 4-methyl benzophenone, p-phenyl benzophenone, 4,4'-bis(dimethylamino)benzophenone, 4-benzoyl-4'-methyl diphenyl sulphide, 4,4'-(tetraethyldiamino)benzophenone, 4,4'-(tetraethyldiamino)benzophenone, benzophenone, 2-hydroxy-1-{4-[4-(2-hydroxy-2-methyl-propionyl)-benzyl]-phenyl}-2-methyl propan-1-one, 1-hydroxycyclohexyl phenyl ketone, 2,2-dimethoxy-2-phenylacetophenone, 4-2-hydroxyethoxy)phenyl-(2-propyl)ketone, camphorquinone and 2,4,6-trimethylbenzophenone.

In a fourteenth embodiment, the invention provides a radiation curable composition of the twelfth embodiment, wherein the liquid photoinitiators are selected from the group consisting of 2,4,6-(trimethylbenzoyl ethoxy, phenyl phosphine)oxide, diethoxy acetophenone, 2-hydroxy 2-methyl-1-phenyl-propane-1-one, methyl phenylglyoxylate and acrylated benzophenone.

In a fifteenth embodiment, the invention provides a radiation curable composition of the twelfth embodiment, wherein the at least one additional photoinitiator is a bis(acyl)phosphine.

In a sixteenth embodiment, the invention provides a radiation curable composition of the twelfth embodiment, wherein the at least one additional photoinitiator is a stabilized bis (acyl)phosphine

DETAILED DESCRIPTION OF THE INVENTION

Throughout this application, the following abbreviations have the indicated meanings:

| | |
|---|---|
| A-189 | γ-mercaptopropyl trimethoxy silane available from Momentive |
| ACCLAIM 4200 | polypropylene glycol, MW = 4200, available from Bayer |
| BAP | bis(acyl)phosphine |
| BAPO | bis(acyl)phosphine oxide |
| BHT | 2,6-di-tert-butyl-4-methylphenol, available from Fitz Chem. |
| DBTDL | dibutyl tin dilaurate, available from OMG Americas |
| HEA | hydroxyethyl acrylate, available from BASF |
| IRGACURE 819 | bis(2,4,6-trimethylbenzoyl)phenylphosphine oxide, available from Ciba Specialty Chemicals (now owned by BASF) |
| IRGANOX 1035 | thiodiethylene bis(3,5-di-tert-butyl-4-hydroxyphenyl)propionate), available from Ciba, Inc. (now owned by BASF) |
| LMBAPO | A mixture of bis(acyl)phosphine oxide and bis(acyl)phosphine |
| MONDUR TDS | 100% 2,4-isomer of toluene diisocyanate, available from Bayer |
| SR-339A | 2-phenoxyethyl acrylate |
| SR-349 | ethoxylated (3) bisphenol A diacrylate, available from Sartomer |
| SR-504D | ethoxylated nonyl phenol acrylate, available from Sartomer |
| TINUVIN 123 | bis(1-octyloxy-2,2,6,6-tetramethyl-4-piperidyl)sebacate, available from Ciba, Inc. (now owned by BASF) |
| TPO | 2,4,6-trimethylbenzoyl diphenyl phosphine oxide |
| TPO-L | 2,4,6-(trimethylbenzoyl ethoxy, phenyl phosphine)oxide |

In this specification a number of terms are used which are well known to a skilled addressee. Nevertheless, for the purposes of clarity a number of terms will be defined.

As used herein, the term unsubstituted means that there is no substituent or that the only substituents are hydrogen.

"Acyl" means an alkyl-CO— group or an aryl-CO— group in which the alkyl or aryl group is as described herein, examples of acyl include acetyl and benzoyl. The alkyl group is preferably a $C_1$-$C_6$ alkyl or optionally substituted aryl group. The group may be a terminal group or a bridging group.

"Alkoxy" refers to an —O-alkyl group in which alkyl is defined herein. Preferably the alkoxy is a $C_1$-$C_6$ alkoxy.

Examples include, but are not limited to, methoxy and ethoxy. The group may be a terminal group or a bridging group.

"Alkyl" as a group or part of a group refers to a straight or branched aliphatic hydrocarbon group, preferably a $C_1$-$C_{18}$ alkyl, more preferably $C_1$-$C_{12}$ alkyl, yet more preferably $C_1$-$C_9$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Alkylthio" refers to an —SR group in which R is an alkyl group as defined herein. The group may be a terminal group or a bridging group.

"Aryl" as a group or part of a group denotes (i) an optionally substituted monocyclic, or fused polycyclic, aromatic carbocyclic (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_5$-$C_7$ cycloalkyl or $C_5$-$C_7$ cycloalkenyl group are fused together to form a cyclic structure, such as tetrahydronaphthyl, indenyl or indanyl. The group may be a terminal group or a bridging group. Other illustrative aryl groups are described herein.

"Halogen" represents chlorine, fluorine, bromine or iodine.

"Heteroalkyl" refers to a straight- or branched-chain alkyl group preferably having from 2 to 14 carbons, more preferably 2 to 10 carbons in the chain, one or more of which has been replaced by a heteroatom selected from S, O, P and N. Exemplary heteroalkyls include alkyl ethers, secondary and tertiary alkyl amines, amides, alkyl sulfides, and the like. The group, may be a terminal group or a bridging group. As used herein, reference to the normal chain when used in the context of a bridging group refers to the direct chain of atoms linking the two terminal positions of the bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulfur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxazine, pyrrole, imidazole, pyrazole, pyridine, pyrazine, pyrimidine, pyridazine, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. The group may be a terminal group or a bridging group.

Applicants have discovered that a liquid bis(acyl)phosphine oxide of formula (I):

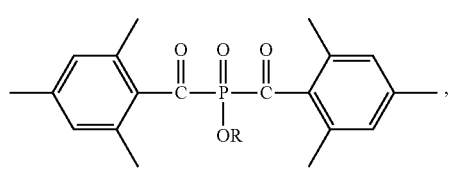

(I)

wherein R is $C_1$-$C_{18}$alkyl, and wherein R is optionally substituted is liquid at 20° C. Having a liquid bis(acyl)phosphine oxide of formula (I): avoids the drawback of solid photoinitiators.

The bis(acyl)phosphine oxide photoinitiators of formula (I) are liquids, thereby avoiding the drawbacks of solid photoinitiators (e.g., BAPO sold commercially as IRGACURE® 819 by Ciba (now owned by BASF) is a solid). For example, liquid bis(acyl)phosphine oxide photoinitiators of the invention exhibit ease of handling, good compatibility with resins and pigments, lack of crystallization problems and no fine dust hazards.

Applicants have discovered that liquid bis(acyl)phosphine photoinitiators of formula (I) can be incorporated into radiation curable optical fiber coating compositions, and radiation curable coating compositions capable of radiation cure on concrete and a radiation curable coating composition capable of radiation cure on metal.

In keeping with an embodiment of the invention, the R group in the bis(acyl)phosphine oxides of formula (I) is $C_1$-$C_{18}$ alkyl wherein R is optionally substituted.

Applicants have found that bis(2,4,6-trimethylbenzoyl) phosphine oxides of formula (I) comprising a $C_1$-$C_{18}$ alkyl group which is optionally substituted provides a photoinitiator in a liquid state.

In some embodiments, the R group of a compound of formula (I) is optionally substituted with one or more substituents. Suitable substituents include, for example, alkyl groups, aryl groups (e.g., phenyl), heteroalkyl groups, and heteroaryl groups. By way of example, when an aryl group is phenyl, the phenyl group can have the following structure:

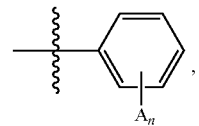

wherein each substituent $A_n$ can be independently any substituent selected from the group consisting of hydrogen, $C_1$-$C_6$alkyl, $C_1$-$C_6$ alkylaryl, $C_1$-$C_6$ alkoxy, $C_5$-$C_{10}$aryl, alkylaryloxy, alkyloxyaryl, heteroalkyl, heteroaryl, heteroalkoxy and halogen, and wherein n represents the number of A substituents on the phenyl ring and n is an integer from 0-5 (i.e., the maximum number of substitution sites on the phenyl group), that is, mono-, di-, tri-, tetra- or penta-substituted, as appropriate. Moreover, the phenyl groups, are optionally substituted in any suitable position, for example, ortho-, meta-, para-substituted.

The skilled artisan recognizes that the value of n varies with the substituent.

In embodiments wherein the R group is substituted, each substituent can be independently any substituent selected from the group consisting of hydrogen, $C_1$-$C_6$ alkyl, $C_1$-$C_6$ alkylaryl, $C_1$-$C_6$ alkoxy, $C_5$-$C_{10}$ aryl, alkylaryloxy, alkyloxyaryl, heteroalkyl, heteroaryl and heteroalkoxy, and n is from 1 to the maximum to number of substitution sites, as appropriate.

Suitable $C_1$-$C_6$ alkyl substituents include, for example, linear and branched $C_1$-$C_6$ alkyl groups, including methyl, ethyl, propyl, isopropyl, butyl, isobutyl, sec-butyl, tert-butyl, pentyl, isopentyl, sec-pentyl, neo-pentyl, hexyl, isohexyl, sec-hexyl, neo-hexyl, and the like.

By way of further illustration, suitable substituents include electron withdrawing groups including, but not limited to halogens, nitrile groups and carbonyl groups. Moreover, suitable substituents also include electron releasing groups including, but not limited to hydroxy groups and amino groups, including substituted amino groups (e.g., —NHR and —NHR$_2$ wherein R is an alkyl group).

Suitable aryl groups and heteroaryl groups include a phenyl group, a naphthyl group, an anthracenyl group, a furanyl group, a benzofuranyl group, an isobenzofuranyl group, a pyrrolyl group, a pyridyl group, a pyrazinyl group, a pyrimidinyl group, a pyridazinyl group, an indolyl group, an isoindolyl group, an imidazolyl group, a pyrazolyl group, a quinolinyl group, an isoquinolinyl group, a quinoxalinyl group, a quinazolinyl group, a cinnolinyl group, a thiophenyl group, a benzothiophenyl group, an acridinyl group, a benzimidazolyl group, an indazolyl group, a benzoxazolyl group, a benzisoxazolyl group, a benzothiazolyl group, a purinyl group and a benzo[c]thiophenyl group.

In an embodiment, the aryl group is a phenyl group, a naphthyl group, or an anthracenyl group.

In an embodiment, the aryl group and/or heteroaryl group is substituted. An illustrative substituted aryl group is, for example, a substituted phenyl group. Suitable substituted phenyl groups include methylphenyl group, ethylphenyl group, dimethylphenyl group, trialkylphenyl group, isopropylphenyl group, tert-butyl phenyl group, methoxy phenyl group, dimethoxyphenyl group, ethoxy phenyl group, diethoxy phenyl group, isopropoxy phenyl group and thiomethoxy phenyl group.

In an embodiment, the trialkylphenyl group is a trimethylphenyl group.

In another embodiment, the trimethylphenyl group is a 2,4,6-trimethylphenyl group.

Suitable alkyl groups include $C_1$-$C_{18}$ alkyl groups, $C_1$-$C_{12}$ alkyl groups, $C_1$-$C_9$ alkyl groups, $C_1$-$C_6$ alkyl groups, and $C_1$-$C_3$ alkyl groups, as known to the skilled artisan.

Suitable heteroalkyl groups include an alkoxy group or an alkylthio group, wherein the alkoxy or alkylthio group is optionally substituted.

In an embodiment, the heteroalkyl group is an alkoxy group. Suitable alkoxy groups include, for example, $C_1$-$C_{18}$ alkoxy groups. In an embodiment, the alkoxy group is selected from $C_1$-$C_{12}$ alkoxy group, or $C_1$-$C_9$ alkoxy groups, or $C_1$-$C_6$ alkoxy groups, or $C_1$-$C_3$ alkoxy groups. Illustrative $C_1$-$C_{18}$ alkoxy groups. Illustrative alkoxy groups include, for example, methoxy, ethoxy, propoxy, isopropoxy, butoxy, isobutoxy, sec-butoxy, pentoxy, hexoxy, heptoxy, octoxy, nonoxy, decoxy, undecoxy and dodecoxy.

In an embodiment, the heteroalkyl group is an alkylthio group. Illustrative alkylthio groups include, for example, $C_1$-$C_6$ alkylthio, such as methylthio, ethylthio, and propylthio. In an embodiment, the alkylthio group is a $C_1$-$C_{18}$ alkylthio.

The inventive bis(acyl)phosphine oxides can be synthesized using any suitable process known to the skilled artisan. A proposed synthetic scheme is depicted herein at Scheme 1. Not wishing to be bound by a particular synthesis, the inventive bis(acyl)phosphine oxides can be prepared by converting solid BAPO (1) to illustrative bis(acyl)phosphine oxides of the invention (e.g., compound (2); Scheme 1).

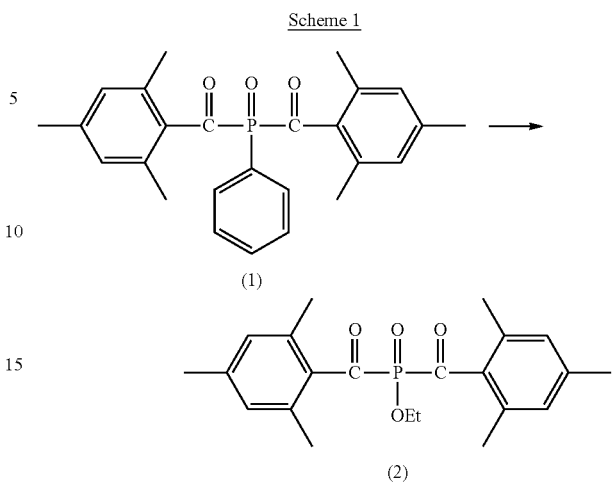

Scheme 1

In another embodiment the invention provides a radiation curable composition comprising a bis(acyl)phosphine oxide as described herein.

The radiation curable compositions of the invention comprise at least one free-radical polymerizable component. The radiation curable compositions of the invention typically comprise an acrylate group as a free-radical polymerizable component. Other suitable free-radical polymerizable components include, for example, methacrylate, acrylamide, methacrylamide, vinyl amide, vinyl ether groups and other ethylenic unsaturated moieties known to the skilled artisan.

In an embodiment, the invention provides a radiation curable optical fiber coating composition comprising a bis(acyl) phosphine oxide of formula (I) and at least one free-radical polymerizable component. The optical fiber coating composition of the invention can be any suitable optical fiber coating composition. In an embodiment the optical fiber coating composition is selected from the group consisting of a primary coating, a secondary coating, an ink coating, an upjacketing coating, a buffer coating and a matrix coating.

In another embodiment, the invention provides a radiation curable coating composition capable of radiation cure on concrete comprising a bis(acyl)phosphine oxide of formula (I) and at least one free-radical polymerizable component.

Commercially available, radiation curable coating compositions for concrete are known to the skilled artisan. For example, see http://www.uvolvecoatings.com/.

In another embodiment, the invention provides a radiation curable coating composition capable of radiation cure on metal comprising a bis(acyl)phosphine of formula (I) and at least one free-radical polymerizable component.

Conventional coating compositions for metal are known to the skilled artisan. For example, see http://www.dsm.com/en_US/html/dsmd/uvention_tube.htm.

In an embodiment, the invention provides a radiation curable optical fiber coating composition or a radiation coating compositions capable of radiation cure on concrete and a coating composition capable of radiation cure on metal wherein the compositions comprise or consists of at least one free-radical polymerizable component and a combination of at least two photoinitiators wherein at least one photoinitiator is a bis(acyl)phosphine oxide of formula (I) and at least one photoinitiator is a conventional photoinitiator (e.g., 2,4,6-trimethylbenzoyl)phenylphosphine oxide.

In keeping with an aspect of the invention, the radiation curable composition is a liquid. In an embodiment the combination of a bis(acyl)phosphine oxide of formula (I) and a conventional photoinitiator is a liquid at a temperature greater than about 15° C.

As used herein, the term "about" means±10% of the stated value.

The radiation curable coating compositions of the invention are designed to be cured by conventional UV lights. However, should it be desirable to cure the instant claimed coating compositions using LED light, Applicants have designed coating compositions which are curable by light generated by a LED source.

The use of ultraviolet mercury arc lamps to emit ultraviolet light suitable to cure radiation curable coatings applied to optical fiber is well known. Ultraviolet arc lamps emit light by using an electric arc to excite mercury that resides inside an inert gas (e.g., argon) environment to generate ultraviolet light which effectuates curing. Alternatively, microwave energy can also be used to excite mercury lamps in an inert gas medium to generate the ultraviolet light. Throughout this patent application, arc excited and microwave excited mercury lamp, plus various additives (ferrous metal, gallium, etc.) modified forms of these mercury lamps are identified as mercury lamps.

However, the use of ultraviolet mercury lamps as a radiation source suffers from several disadvantages including environmental concerns from mercury and the generation of ozone as a by-product. Further, mercury lamps typically have lower energy conversion ratio, require warm-up time, generate heat during operation, and consume a large amount of energy when compared with LED. In the production of coated optical fiber, the heat generated by the UV mercury lamps can negatively impact the liquid coating in that if the coating is not formulated to avoid the presence of volatiles, those volatiles may be excited and deposit upon the quartz tube surface, blocking the UV rays from irradiating the liquid coating on the glass fiber which inhibits the curing of the liquid coating to a solid. In addition, mercury lamps are characterized by a broad spectral output, in addition to the UV radiation, much of which is not useful for curing and can damage substrates and presents hazards to personnel. Accordingly, alternative radiation sources are being investigated.

Light emitting diodes (LEDs) are semiconductor devices which use the phenomenon of electroluminescence to generate light. LEDs consist of a semiconducting material doped with impurities to create a p-n junction capable of emitting light as positive holes join with negative electrons when voltage is applied. The wavelength of emitted light is determined by the materials used in the active region of the semiconductor. Typical materials used in semiconductors of LEDs include, for example, elements from Groups 13 (III) and 15 (V) of the periodic table. These semiconductors are referred to as III-V semiconductors and include, for example, GaAs, GaP, GaAsP, AlGaAs, InGaAsP, AlGaInP and InGaN semiconductors. Other examples of semiconductors used in LEDs include compounds from Group 14 (IV-IV semiconductor) and Group 12-16 (II-VI). The choice of materials is based on multiple factors including desired wavelength of emission, performance parameters and cost.

Early LEDs used gallium arsenide (GaAs) to emit infrared (IR) radiation and low intensity red light. Advances in materials science have led to the development of LEDs capable of emitting light with higher intensity and shorter wavelengths, including other colors of visible light and UV light. It is possible to create LEDs that emit light anywhere from a low of about 100 nm to a high of about 900 nm. Currently, known LED UV light sources emit light at wavelengths between about 300 and about 475 nm, with 365 nm, 390 nm and 395 nm being common peak spectral outputs. See textbook, "Light-Emitting Diodes" by E. Fred Schubert, $2^{nd}$ Edition, © E. Fred Schubert 2006, published by Cambridge University Press. When using LED lamps for curing coating compositions, the photoinitiator is the coating composition is selected to be responsive to the wavelength of light emitted by the LED lamp.

LED lamps offer advantages over mercury lamps in curing applications. For example, LED lamps do not use mercury to generate UV light and are typically less bulky than mercury UV arc lamps. In addition, LED lamps are instant on/off sources requiring no warm-up time, which contributes to LED lamps' low energy consumption. LED lamps also generate much less heat, with higher energy conversion efficiency, have longer lamp lifetimes, and are essentially monochromatic emitting a desired wavelength of light which is governed by the choice of semiconductor materials employed in the LED.

Several manufacturers offer LED lamps for commercial curing applications. For example, Phoseon Technology, Summit UV, Honle UV America, Inc., IST Metz GmbH, Jenton International Ltd., Lumios Solutions Ltd., Solid UV Inc., Seoul Optodevice Co., Ltd, Spectronics Corporation, Luminus Devices Inc., and Clearstone Technologies, are some of the manufacturers currently offering LED lamps for curing ink-jet printing compositions, PVC floor coating compositions, metal coating compositions, plastic coating composition and adhesive compositions.

LED curing of radiation curable coatings for optical fiber is described and claimed in U.S. Provisional Patent Application 61/287567, filed 17 Dec. 2009 and in PCT Patent Application PCT/US2010/60652 filed 16 Dec. 2010, both entitled "D1429 BT LED Curing of Radiation Curable Optical Fiber Coating Compositions", which are both incorporated herein by reference, in their entirety.

In an embodiment, the invention provides a radiation curable composition wherein the composition is curable by UV light generated by a conventional UV light source.

In another embodiment, the invention provides a radiation curable composition wherein the composition is curable by light generated by a LED light source.

In an embodiment, the present invention provides a radiation curable optical fiber coating composition. As used herein, "optical fiber" coating refers to primary coatings (i.e., inner primary coatings), secondary coatings (i.e., outer primary coatings), ink coatings, up-jacketing coatings, matrix coatings and cabling (bundling) materials. Optical fiber coating compositions of the invention comprise or consist of at least one radiation-curable oligomer, at least one radiation-curable monomer diluent, at least one liquid bis(acyl)phosphine photoinitiator of formula (I), and additives. The details of radiation curable optical fiber coating compositions are described in, for example, U.S. Pat. No. 6,136,880 to Snowwhite et al., which is incorporated herein by reference in its entirety.

Examples of radiation-curable inner primary coatings are disclosed in U.S. Pat. No. 5,336,563 to Coady et al. and of outer primary coatings (e.g., secondary coatings) in U.S. Pat. No. 4,472,019 to Bishop et al. Additional aspects of optical fiber coating technology are disclosed in, for example, U.S. Pat. No. 5,595,820 to Szum; U.S. Pat. No. 5,199,098 to Nolan et al.; U.S. Pat. No. 4,923,915 to Urruti et al.; U.S. Pat. No. 4,720,529 to Kimura et al.; and U.S. Pat. No. 4,474,830 to Taylor et al., each of which is incorporated herein by reference in their entirety.

The article, "UV-CURED POLYURETHANE-ACRYLIC COMPOSITIONS AS HARD EXTERNAL LAYERS OF TWO-LAYER PROTECTIVE COATINGS FOR OPTICAL FIBRES", authored by W. Podkoscielny and B. Tarasiuk, Polim.Tworz.Wielk, Vol. 41, Nos. 7/8, p. 448-55, 1996, NDN-131-0123-9398-2, describes studies of the optimization of synthesis of UV-cured urethane-acrylic oligomers and their use as hard protective coatings for optical fibers. Polish-made oligoetherols, diethylene glycol, toluene diisocyanate (Izocyn T-80) and isophorone diisocyanate in addition to hydroxyethyl and hydroxypropyl(meth)acrylates were used for the synthesis. Active diluents (butyl acrylate, 2-ethylhexyl acrylate and 1,4-butanediol acrylate or mixtures of these) and 2,2-dimethoxy-2-phenylacetophenone as a photoinitiator were added to these urethane-acrylic oligomers which had polymerization-active double bonds. The compositions were UV-irradiated in an oxygen-free atmosphere. IR spectra of the compositions were recorded, and some physical and chemical and mechanical properties (density, molecular weight, viscosity as a function of temperature, refractive index, gel content, glass transition temperature, Shore hardness, Young's modulus, tensile strength, elongation at break, heat resistance and water vapor diffusion coefficient) were determined before and after curing.

The article, "PROPERTIES OF ULTRAVIOLET CURABLE POLYURETHANE-ACRYLATES", authored by M. Koshiba; K. K. S. Hwang; S. K. Foley; D. J. Yarusso; and S. L. Cooper; published in J. Mat. Sci., 17, No. 5, May 1982, p. 1447-58; NDN-131-0063-1179-2; described a study that was made of the relationship between the chemical structure and physical properties of UV cured polyurethane-acrylates based on isophorone diisocyanate and TDI. The two systems were prepared with varying soft segment molecular weight and cross linking agent content. Dynamic mechanical test results showed that one- or two-phase materials might be obtained, depending on soft segment molecular weight. As the latter increased, the polyol Tg shifted to lower temperatures. Increasing using either N-vinyl pyrrolidone (NVP) or polyethylene glycol diacrylate (PECDA) caused an increase in Young's modulus and ultimate tensile strength. NVP cross linking increased toughness in the two-phase materials and shifted the high temperature Tg peak to higher temperatures, but PEGDA did not have these effects. Tensile properties of the two systems were generally similar.

Typically in the manufacture of radiation curable coatings for use on optical fiber, isocyanates are used to make urethane oligomers. In many references, including U.S. Pat. No. 7,135, 229, "RADIATION-CURABLE COATING COMPOSITION", Issued Nov. 14, 2006, assigned to DSM IP Assets B.V., (column 7, lines 10-32) teaching is provided to guide the person of ordinary skill in the art how to synthesize urethane oligomers: polyisocyanates suitable for use in making compositions of the present invention can be aliphatic, cycloaliphatic or aromatic and include diisocyanates, such as 2,4-toluene diisocyanate, 2,6-toluene diisocyanate, 1,3-xylene diisocyanate, 1,4-xylylene diisocyanate, 1,5-naphthalene diisocyanate, m-phenylene diisocyanate, p-phenylene diisocyanate, 3,3'-dimethyl-4,4'-diphenylmethane diisocyanate, 4,4'-diphenylmethane diisocyanate, 3,3'-dimethylphenylene diisocyanate, 4,4'-biphenylene diisocyanate, 1,6-hexane diisocyanate, isophorone diisocyanate, methylene bis(4-cyclohexyl)isocyanate, 2,2,4-trimethylhexamethylene diisocyanate, bis(2-isocyanate-ethyl)fumarate, 6-isopropyl-1,3-phenyl diisocyanate, 4-diphenylpropane diisocyanate, lysine diisocyanate, hydrogenated diphenylmethane diisocyanate, hydrogenated xylylene diisocyanate, tetramethylxylylene diisocyanate and 2,5(or 6)-bis(isocyanatomethyl)-bicyclo[2.2.1]heptane. Among these diisocyanates, 2,4-toluene diisocyanate, isophorone diisocyanate, xylene diisocyanate, and methylene bis(4-cyclohexylisocyanate) are particularly preferred. These diisocyanate compounds are used either individually or in combination of two or more.

In many of these compositions, use is made of a urethane oligomer having reactive termini and a polymer backbone. Further, the compositions generally comprise reactive diluents, photoinitiators to render the compositions UV-curable, and other suitable additives.

Published PCT Patent Application WO 2205/026228 A1, published Sep. 17, 2004, "Curable Liquid Resin Composition", with named inventors Sugimoto, Kamo, Shigemoto, Komiya and Steeman, describes and claims a curable liquid resin composition comprising: (A) a urethane(meth)acrylate having a structure originating from a polyol and a number average molecular weight of 800 g/mol or more, but less than 6000 g/mol, and (B) a urethane(meth)acrylate having a stricture originating from a polyol and a number average molecular weight of 6000 g/mol or more, but less than 20,000 g/mol, wherein the total amount of the component (A) and component (B) is 20-95 wt % of the curable liquid resin composition and the content of the component (B) is 0.1-30 wt % of the total of the component (A) and component (B).

Many materials have been suggested for use as the polymer backbone for the urethane oligomer. For example, polyols such as hydrocarbon polyols, polyether polyols, polycarbonate polyols and polyester polyols have been used in urethane oligomers. Polyester polyols are particularly attractive because of their commercial availability, oxidative stability and versatility to tailor the characteristics of the coating by tailoring the backbone. The use of polyester polyols as the backbone polymer in a urethane acrylate oligomer is described, for example, in U.S. Pat. Nos. 5,146,531, 6,023, 547, 6,584,263, 6,707,977, 6,775,451 and 6,862,392, as well as European Patent 539 030 A.

Concern over the cost, use and handling of urethane precursors has lead to the use of urethane-free oligomers in coating compositions. For example, urethane-free polyester acrylate oligomers have been used in radiation-curable coating compositions for optical glass fibers. Japanese Patent 57-092552 (Nitto Electric) discloses all optical glass fiber coating material comprising a polyester di(meth)acrylate where the polyester backbone has an average molecular weight of 300 or more. German Patent Application 04 12 68 60 A1 (Bayer) discloses a matrix material for a three-fiber ribbon consisting of a polyester acrylate oligomer, 2-(N-butyl-carbamyl)ethyl acrylate as reactive diluent and 2-hydroxy-2-methyl-1-phenyl-propan-1-one as photoinitiator. Japanese Patent Application No. 10-243227 (Publication No. 2000-072821) discloses a liquid curable resin composition comprising a polyester acrylate oligomer which consists of a polyether diol end-capped with two diacids or anhydrides and terminated with hydroxy ethyl acrylate. U.S. Pat. No. 6,714, 712 B2 discloses a radiation curable coating composition comprising a polyester and/or alkyd(meth)acrylate oligomer comprising a polyacid residue or an anhydride thereof, optionally a reactive diluent, and optionally a photoinitiator. Also, Mark D. Soucek and Aaron H. Johnson disclose the use of hexahydrophthalic acid for hydrolytic resistance in "New Intramolecular Effect Observed for Polyesters: An Anomeric Effect," JCT Research, Vol. 1, No. 2, p. 111 (April 2004).

The radiation curable compositions of the invention can comprise more than one photoinitiator. In addition to the liquid bis(acyl)phosphine oxides of formula (I), the radiation curable compositions can further comprise any suitable photoinitiator. Illustrative solid bis(acyl)phosphine oxides which can be included are, for example, bis-(2,4,6-trimethylbenzoyl)-phenylphosphine oxide (hereinafter abbreviated as "BTBTO"); bis-(2,6-dimethylbenzoyl)-phenylphosphine oxide; bis(benzoyl)phenylphosphine oxide; bis-(2,6-dimethoxybenzoyl)phenylphosphine oxide; and bisbenzoyl (2,4,6-trimethyl)phenylphosphine oxide.

Photoinitiators other than those represented by formula (I) can be jointly used as a photoinitiator in the liquid curable resin composition of the present invention. Also, a photosensitizer may be added as required. Suitable photosensitizers are known to the skilled artisan and include anthraquinones, such as 2-methylanthraquinone, 2-ethylanthraquinone, 2-tert-butylanthraquinone, 1-chloroanthraquinone, and 2-amylanthraquinone, thioxanthones and xanthones, such as isopropyl thioxanthone, 2-chlorothioxanthone, 2,4-diethylthioxanthone, and 1-chloro-4-propoxythioxanthone, methyl benzoyl formate (DAROCUR™ MBF from Ciba (now owned by BASF)), methyl-2-benzoyl benzoate (CHIVACURE™ OMB from Chitec), 4-benzoyl-4'-methyl diphenyl sulfide (CHIVACURE™ BMS from Chitec), 4,4'-bis(diethylamino)benzophenone (CHIVACURE™ EMK from Chitec).

Examples of the photoinitiator which can be jointly used include 1-hydroxycyclohexyl phenyl ketone, 2,2-dimethoxy-2-phenylacetophenone, xanthone, fluorenone, benzaldehyde, fluorene, anthraquinone, triphenylamine, carbazole, 3-methylacetophenone, 4-chlorobenzophenone, 4,4'-dimethoxybenzophenone, 4,4'-diaminobenzophenone, Michler's ketone, benzoinpropyl ether, benzoinethyl ether, benzyldimethyl ketal, 1-(4-isopropylphenyl)-2-hydroxy-2-methylpropane-1-one, 2-hydroxy-2-methyl-1-phenylpropane-1-one, thioxanthone, diethylthioxanthone, 2-isopropylthioxanthone, 2-chlorothioxanthone, 2-methyl-1-[4-(methylthio) phenyl]-2-morpholino-propane-1-one, 2,4,6-trimethylbenzoyldiphenylphosphine oxide, bis-(2,6-dimethoxybenzoyl)-2,4,4-trimethylpentylphosphine oxide and commercially available products such as IRGACURE® 184, 369, 651, 500, 907, 1700, 1850, (Ciba Specialty Chemicals, Inc. (now owned by BASF)), LUCIRIN™ TPO (BASF), DAROCUR™ 1173 (Ciba Specialty Chemicals, Inc., now owned by BASF), EBECRYL™ P36 (Cytec Surface Specialties, Inc.), and the like.

Examples of suitable solid photoinitiators (solid photoinitiators are solid at 20° C.) that can be further included in radiation curable compositions comprising the inventive bis (acyl)phosphine oxides include 4-methyl benzophenone, p-phenyl benzophenone, 4,4'-bis(dimethylamino)benzophenone, 4-benzoyl-4'-methyl diphenyl sulphide, 4,4'-(tetraethyldiamino)benzophenone, 4,4'-(tetraethyldiamino)benzophenone, benzophenone, 2-hydroxy-1-{4-[4-(2-hydroxy-2-methyl-propionyl)-benzyl]-phenyl}-2-methyl-propan-1-one, 1-hydroxycyclohexyl phenyl ketone, 2,2-dimethoxy-2-phenylacetophenone, 4-(2-hydroxyethoxy)phenyl-(2-propyl)ketone, camphorquinone and 2,4,6-trimethylbenzophenone.

Examples of suitable liquid photoinitiators (liquid photoinitiators t are liquid at 20° C.) that can be further included in radiation curable compositions comprising the inventive bis (acyl)phosphine oxides include 2,4,6-(trimethylbenzoyl ethoxy, phenyl phosphine)oxide, diethoxy acetophenone, 2-hydroxy-2-methyl-1-phenyl-propane-1-one, methyl phenylglyoxylate and acrylated benzophenone.

The photoinitiator generally is contained in the composition in a concentration of 0.05 wt. % or higher, preferably more than 0.1 wt. %, and more preferred, more than 1 wt. %. Generally, the amount will be about 15 wt. % or less, preferably about 10 wt. % or less and more preferably 5 wt. % or less to improve the curing speed of the liquid curable resin composition and the durability of the cured product. The amount will vary depending on the application. In considering an "effective amount", several factors can be considered including the nature of the other components in the composition, the type of material (e.g., inner or outer primary coating), the film thickness, the amount of non-yellowing which can be tolerated, the amount of surface versus through cure, whether the composition is clear or colored, and the like. The amount will be selected to provide for an optimal balance of properties for a particular application, key properties including good cure speed, non-yellowing character, and lack of harmful crystallization.

It is preferred to exclude atmospheric oxygen during the polymerization, which may be effected by $N_2$ purge, or by adding paraffin or similar wax-like substances which, at the onset of polymerization, migrate to the surface owing to lack of solubility in the polymer and form a transparent film which prevents air from entering the system. The inhibiting effect of atmospheric oxygen may also be overcome by combining accelerators (or synergists) with the photoinitiators. Examples of such accelerators or photosensitizers include secondary and/or tertiary amines, such as, dimethylethanolamine, triethanolamine, benzyldimethylamine, di methylaminoethyl acrylate, N-phenylglycine, N-methyl-N-phenylglycine, triethylamine, diethylamine, N-methyldiethanolamine, ethanolamine, 4-dimethylaminobenzoic acid, methyl 4-dimethylamino benzoate, ethyl 4-dimethylaminobenzoate, isoamyl 4-dimethylamino benzoate, 2-ethylhexyl-4-dimethylaminobenzoate, acrylated amines, and commercially available products such as MDEA EBECRYL™ P104, 115, 7100, ADDITOL™ EHA, and ADDITOL™ EPD (Cytec Surface Specialties, Inc.).

The radiation curable compositions of the invention, including embodiments wherein the radiation curable composition comprises more than one photoinitiator, are liquid compositions.

The following examples further illustrate the invention but, of course, should not be construed as in any way limiting its scope.

EXAMPLE 1

This example illustrates the synthesis of a liquid bis(2,4,6-trimethylbenzoyl)-n-butoxyphosphine oxide, that is, a bis(acyl)phosphine oxide of the invention.

Butyllithium (140.6 mL, 0.225 mol, 1.6 M) is added dropwise under a nitrogen atmosphere at 0° C. over a period of 30 minutes to a solution of diisopropylamine (31.9 mL, 0.225 mol) in 80 mL of tetrahydrofuran. This solution is added dropwise at −30° C. over a period of 90 minutes to a solution of 2,4,6-trimethylbenzoyl chloride (20.5 g, 0.112 mol) and di-n-butyl hydrogen phosphite (19.8 g, 0.102 mol) in 200 mL of tetrahydrofuran. After stirring the mixture for 2 h at −30° C., toluene (80 mL) is added with stirring. The solution is washed with water at room temperature and the aqueous phase is separated. The organic phase is dried with magnesium sulfate, filtered, and concentrated using a rotary evaporator.

The product is dissolved in tetrahydrofuran (200 mL) at room temperature and zinc bromide (22.5 g, 0.1 mol) is added. To the mixture is added dropwise 2,4,6-trimethylbenzoyl chloride (20.7, 0.113 mol). After 4 h, the reaction mixture is diluted with toluene (200 mL) and then filtered. The filtrate is washed with water (400 mL) and the phases separated. The organic phase is dried with magnesium sulfate, filtered, and concentrated using a rotary evaporator.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A liquid bis(acyl)phosphine oxide of formula (I):

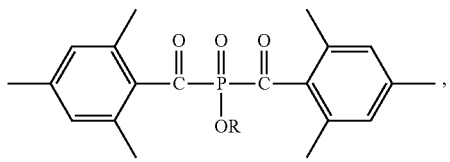

(I)

wherein R is $C_1$-$C_{18}$ alkyl, and wherein R is optionally substituted.

2. The bis(acyl)phosphine oxide of claim 1, wherein R is $C_1$-$C_6$ alkyl.

3. The bis(acyl)phosphine oxide of claim 2, wherein R is selected from the group consisting of methyl, ethyl, n-propyl, 2-propyl, n-butyl, sec-butyl, t-butyl, and hexyl.

4. The bis(acyl)phosphine oxide of claim 2, wherein R is $C_1$-$C_3$ alkyl.

5. The bis(acyl)phosphine oxide of claim 4, wherein R is selected from the group consisting of methyl, ethyl and n-propyl.

6. The bis(acyl)phosphine oxide of claim 5, wherein R is ethyl.

7. A radiation curable composition comprising the bis(acyl)phosphine oxide of claim 1 and at least one free-radical polymerizable component.

8. The radiation curable composition of claim 7, wherein said composition is selected from the group consisting of an optical fiber coating composition and a coating composition capable of radiation cure on concrete and a coating composition capable of radiation cure on metal.

9. The radiation curable composition of claim 8, wherein said composition is an optical fiber coating composition.

10. The radiation curable composition of claim 8, wherein said composition is a coating capable of radiation cure on concrete.

11. The radiation curable composition of claim 8, wherein said composition is a coating capable of radiation cure on metal.

12. The radiation curable composition of claim 7, wherein the composition is curable by UV light generated by a conventional UV light source.

13. The radiation curable composition of claim 7, wherein the composition is curable by light generated by a LED light source.

14. The radiation curable composition of claim 7, wherein the composition further comprises at least one additional photoinitiator.

15. The radiation curable composition of claim 14, wherein the at least one additional photoinitiator is selected from the group consisting of solid photoinitiators and liquid photoinitiators.

16. The radiation curable composition of claim 15, wherein the solid photoinitiators are selected from the group consisting of 4-methyl benzophenone, p-phenyl benzophenone, 4,4'-bis(dimethylamino)benzophenone, 4-benzoyl-4'-methyl diphenylsulphide, 4,4'-(tetraethyldiamino)benzophenone, 4,4'-(tetraethyldiamino)benzophenone, benzophenone, 2-hydroxy-1-{4-[4-(2-hydroxy-2-methyl-propionyl)-benzyl]-phenyl}-2-methyl-propan-1-one, 1-hydroxycyclohexyl phenyl ketone, 2,2-dimethoxy-2-phenylacetophenone, 4-(2-hydroxyethoxy)phenyl-(2-propyl)ketone, camphorquinone and 2,4,6-trimethylbenzophenone.

17. The radiation curable composition of claim 15, wherein the liquid photoinitiators are selected from the group consisting of 2,4,6-(trimethylbenzoyl ethoxy, phenyl phosphine) oxide, diethoxy acetophenone, 2-hydroxy-2-methyl-1-phenyl-propane-1-one, methyl phenylglyoxylate and acrylated benzophenone.

18. The radiation curable composition of claim 15, wherein the at least one additional photoinitiator is a bis(acyl)phosphine.

19. The radiation curable composition of claim 15, wherein the at least one additional photoinitiator is a stabilized bis(acyl)phosphine.

* * * * *